US010918308B2

(12) United States Patent
Esposito, Jr.

(10) Patent No.: US 10,918,308 B2
(45) Date of Patent: *Feb. 16, 2021

(54) RESPIRATORY COMPONENT MEASUREMENT SYSTEM INCLUDING A SENSOR FOR DETECTING ORIENTATION OR MOTION

(75) Inventor: Anthony J. Esposito, Jr., Cheshire, CT (US)

(73) Assignee: Koninklijke Philips N.V., Eindhoven (NL)

(*) Notice: Subject to any disclaimer, the term of this patent is extended or adjusted under 35 U.S.C. 154(b) by 1787 days.

This patent is subject to a terminal disclaimer.

(21) Appl. No.: 12/119,915

(22) Filed: May 13, 2008

(65) Prior Publication Data

US 2008/0283062 A1   Nov. 20, 2008

Related U.S. Application Data

(60) Provisional application No. 60/938,818, filed on May 18, 2007.

(51) Int. Cl.
*A61B 5/087* (2006.01)
*A61B 5/08* (2006.01)
(Continued)

(52) U.S. Cl.
CPC .............. *A61B 5/087* (2013.01); *A61B 5/061* (2013.01); *A61B 5/08* (2013.01); *A61B 5/082* (2013.01); *A61B 5/097* (2013.01); *A61M 16/085* (2014.02); *A61M 16/0816* (2013.01); *A61M 16/0858* (2014.02); *A61M 16/161* (2014.02); *G01F 1/36* (2013.01); *A61B 5/0833* (2013.01);
(Continued)

(58) Field of Classification Search
USPC ........... 128/200.24, 202.22, 202.27, 204.21, 128/204.23; 600/532, 538
See application file for complete search history.

(56) References Cited

U.S. PATENT DOCUMENTS 4,668,846 A * 5/1987 Klumpp ................. 200/61.45 R
4,862,898 A * 9/1989 Hudimac, Jr. ................ 600/538
(Continued)

FOREIGN PATENT DOCUMENTS

JP    2002328134 A    11/2002
JP    2004136105 A    5/2004
(Continued)

OTHER PUBLICATIONS

Gordon et al. Test Results with the EasyQ River Flow Sensor. Nortek technical note. Apr. 14, 2000, pp. 1-7.*
U.S. Appl. No. 60/808,312, Russell.

*Primary Examiner* — Kathryn E Ditmer
(74) *Attorney, Agent, or Firm* — Daniel H. Brean

(57) ABSTRACT

A respiratory component measurement system that includes an airway adapter adapted to be placed in fluid communication with an airway of a patient and a sensor element in physical communication with the airway adapter. The sensor element is adapted to detect an orientation related characteristic of the airway adapter, a motion related characteristic of the airway adapter, or both. A respiratory component sensor is also adapted to be disposed on the airway adapter so as to measure a characteristic associated with a flow of gas through the airway adapter.

33 Claims, 5 Drawing Sheets

(51) Int. Cl.
  *A61B 5/097* (2006.01)
  *G01F 1/36* (2006.01)
  *A61M 16/08* (2006.01)
  *A61M 16/00* (2006.01)
  *A61M 16/10* (2006.01)
  *A61B 5/06* (2006.01)
  *A61M 16/16* (2006.01)
  *A61B 5/083* (2006.01)

(52) U.S. Cl.
  CPC .... *A61B 5/0836* (2013.01); *A61M 2016/0027* (2013.01); *A61M 2016/0036* (2013.01); *A61M 2016/102* (2013.01); *A61M 2016/103* (2013.01); *A61M 2016/1025* (2013.01); *A61M 2016/1035* (2013.01); *A61M 2205/18* (2013.01); *A61M 2205/276* (2013.01); *A61M 2205/332* (2013.01); *A61M 2205/3306* (2013.01); *A61M 2205/3317* (2013.01); *A61M 2205/3368* (2013.01); *A61M 2205/581* (2013.01); *A61M 2205/583* (2013.01); *A61M 2230/432* (2013.01); *A61M 2230/435* (2013.01); *A61M 2230/437* (2013.01)

(56) References Cited

U.S. PATENT DOCUMENTS

| | | | |
|---|---|---|---|
| 4,932,269 A * | 6/1990 | Cammarata et al. | 73/861.61 |
| 5,088,332 A | 2/1992 | Merilainen et al. | |
| 5,373,858 A | 12/1994 | Rose | |
| 5,535,633 A | 7/1996 | Kofoed et al. | |
| 5,626,129 A * | 5/1997 | Klimm et al. | 128/202.22 |
| 5,693,944 A | 12/1997 | Rich | |
| 6,216,692 B1 * | 4/2001 | Todokoro et al. | 128/205.23 |
| 6,255,962 B1 * | 7/2001 | Tanenhaus et al. | 340/870.05 |
| 6,301,795 B1 * | 10/2001 | Kang | 33/366.12 |
| 6,312,389 B1 | 11/2001 | Kofoed et al. | |
| 6,691,579 B2 | 2/2004 | Orr et al. | |
| 6,935,338 B1 | 8/2005 | Triunfo, Jr. | |
| 6,954,702 B2 | 10/2005 | Pierry et al. | |
| 7,059,322 B2 | 6/2006 | Rich et al. | |
| 7,335,164 B2 | 2/2008 | Mace et al. | |
| 7,409,871 B2 * | 8/2008 | Wang et al. | 73/861.01 |
| 7,654,146 B2 | 2/2010 | Orr et al. | |
| 7,684,931 B2 | 3/2010 | Pierry et al. | |
| 2002/0029003 A1 | 3/2002 | Mace et al. | |
| 2004/0013570 A1 * | 1/2004 | Labuda et al. | 422/82.08 |
| 2004/0163648 A1 * | 8/2004 | Burton | 128/204.21 |
| 2005/0043607 A1 | 2/2005 | Comanducci | 600/407 |
| 2005/0065448 A1 | 3/2005 | Stahmann et al. | 600/529 |
| 2006/0130838 A1 * | 6/2006 | Lee et al. | 128/205.23 |
| 2006/0145078 A1 | 7/2006 | Russell | |
| 2006/0245078 A1 | 11/2006 | Kawamura | |
| 2006/0249160 A1 * | 11/2006 | Scarberry et al. | 128/207.13 |
| 2006/0264762 A1 * | 11/2006 | Starr | 600/483 |
| 2007/0051185 A1 | 3/2007 | DiMatteo et al. | |
| 2007/0062528 A1 * | 3/2007 | Heinonen et al. | 128/204.21 |
| 2008/0125700 A1 * | 5/2008 | Moberg et al. | 604/67 |
| 2008/0184799 A1 * | 8/2008 | Phan Le et al. | 73/514.31 |
| 2008/0190436 A1 * | 8/2008 | Jaffe et al. | 128/207.18 |
| 2008/0204218 A1 * | 8/2008 | Tupman et al. | 340/501 |
| 2008/0229846 A1 * | 9/2008 | Grotzer | 73/861.18 |
| 2008/0283062 A1 | 11/2008 | Esposito | |
| 2009/0199855 A1 * | 8/2009 | Davenport | 128/204.23 |
| 2010/0077866 A1 * | 4/2010 | Graboi et al. | 73/861.61 |

FOREIGN PATENT DOCUMENTS

| | | |
|---|---|---|
| JP | 2007117601 A | 5/2007 |
| WO | WO 2006111904 A1 * | 10/2006 |

* cited by examiner

RESPIRATORY COMPONENT MEASUREMENT SYSTEM INCLUDING A SENSOR FOR DETECTING ORIENTATION OR MOTION

CROSS-REFERENCE TO RELATED APPLICATIONS

This application claims priority under 35 U.S.C. § 119(e) from provisional U.S. patent application Ser. No. 60/938,818, filed May 18, 2007, the contents of which are incorporated herein by reference.

BACKGROUND OF THE INVENTION

1. Field of the Invention

The present invention relates to a respiratory component measurement system, and, in particular, to a respiratory component measurement system that includes the ability to detect an orientation related characteristic, a motion related characteristic, or both of an airway adapter used in such a system.

2. Description of the Related Art

Respiratory component sensors, which include, but are not limited to, gas constituent sensors and gas flow sensors, are widely used and may be found in monitoring devices and therapeutic devices, such as ventilators and pressure support systems, such as CPAP machines.

Respiratory gas measurement systems typically comprise gas sensing, measurement, processing, communication, and display functions. They are considered to be either diverting, which is also referred to as a sidestream gas measurement system, or non-diverting, which is referred to as a mainstream gas measurement system. A diverting (sidestream) gas measurement system transports a portion of the sampled gases from the sampling site, which is typically an airway adapter in a breathing circuit or the patient's airway, through a sampling tube, to the gas sensor where the constituents of the gas are measured. A non-diverting (mainstream) gas measurement system does not transport gas away from the breathing circuit or airway, but measures the gas constituents passing through the airway adapter. An example of a mainstream gas airway adapter is shown in U.S. Pat. No. 5,693,944, and an example of a sidestream gas sampling airway adapter is shown in U.S. Pat. No. 6,935,338.

Conventional mainstream gas measurement systems include gas sensing/measurement components and signal processing required to convert the detected or measured signal, i.e., voltage, into a value, such as transmittance, that may be used by a host system to output a gas constituent measurement. In a mainstream gas measurement system, the gas sensing/measurement components are coupled to a sample cell, which is usually integrated with the airway adapter or is considered part of the airway adapter. The airway adapter is placed in series in the breathing circuit so that gas flowing in the breathing circuit also flow through the airway adapter.

In either a mainstream or sidestream gas measurement system, the gas sensing/measurement components are those required to output a signal corresponding to a property of the gas being measured. This signal is typically provided to a processor that converts the signal to a gas constituent measurement. The processor may be located in the same housing as the gas sensing/measurement components or may be located remote from the gas sensing/measurement components. In the latter case, a communication link is provided to provide that signal produced by the gas sensing/measurement components to the processor.

In a mainstream gas measurement system, placement of the sample cell, and hence the gas sensing/measurement components, directly in series in the breathing circuit results in a "crisp" waveform that reflects in real-time the partial pressure of the measured gas, such as carbon dioxide or oxygen, within the airway. The sample cell being located in the respiratory gas stream also obviates the need for gas sampling and scavenging, which is required in a sidestream gas measurement system.

Gas flow measurement systems measure the rate of flow of gas. Such flow measurement systems have utilized a variety of different technologies to meet the demanding requirements of the clinical and practical environments in which they are used. Among the flow measurement approaches that have been used for on-airway monitoring are:

1) Differential Pressure—measures the pressure drop or pressure differential across a resistance to flow;
2) Spinning Vane—counts the revolutions of a vane placed in the flow path
3) Hot Wire Anemometer—measures the cooling of a heated wire due to airflow passing around the wire;
4) Ultrasonic Doppler—measures the frequency shift of an ultrasonic beam as it passes through the flowing gas;
5) Vortex Shedding—counts the number of vortices that are shed as the gas flows past a strut placed in the flow stream; and
6) Time of Flight—measures the arrival time of an impulse of sound or heat created upstream to a sensor placed downstream.

With each of the different gas flow measurement approaches, the physical layout or configuration of the airway adapter requirements vary. For example, for performing a differential pressure measurement, two pressure sensing ports are typically placed across a flow restriction, also known as a flow element, so that the pressure drop across the flow element may be measured. An example of a differential pressure flow airway adapter is shown in U.S. Pat. No. 5,535,633. For ultrasonic flow measurement approaches, two windows are placed in the airway adapter, so that the ultrasonics beam interrogate the flow in an acute angle as possible with the direction of flow.

It should also be noted that airway adapters that combine different measurements, such as flow and gas measurements, in a single component are also available. Examples of an airway adapter that include the combination of a mainstream gas measurement system and a flow measurement system are shown in U.S. Pat. No. 6,312,389 and U.S. patent application Ser. No. 09/841,451 (publication no. 2002/0029003A1). The contents of which are incorporated herein by reference. An example of a combination mainstream flow sensor and a sidestream gas sampling airway adapter is shown in U.S. Pat. No. 5,088,332. The content of which is also incorporated herein by reference.

Ensuring that such sensors operate properly and produce a reliable output is of importance given that such sensors are used to monitor a physiological condition of a patient. To this end, it is known to protect against the accumulation of material, such as condensation, water, and sputum, on the measurement components, such as the windows used for IR gas measurements, film used for luminescence sensing based gas measurements, flow sensing components, diaphragms for pressure measurements, wire filaments for thermal measurements, and windows for optical or ultrasonic measurements. For example, filters have used to remove moisture and particulates from the flow of gas being delivered to the measurement components. In other situations, the measurement components are configured to be relatively robust so that they function adequately even in the presence of such materials.

SUMMARY OF THE INVENTION

Accordingly, it is an object of the present invention to provide a respiratory component measurement system that overcomes the shortcomings of conventional respiratory component measurement systems. This object is achieved according to one embodiment of the present invention by providing a respiratory component measurement system that includes an airway adapter adapted to be placed in fluid communication with an airway of a patient, and a sensor element in physical communication with the airway adapter. The sensor element detects an orientation related characteristic of the airway adapter, a motion related characteristic of the airway adapter of the airway adapter, or both. The respiratory component measurement system also includes a respiratory component sensor adapted to be disposed on the airway adapter. The respiratory component sensor measures a parameter associated with a flow of gas through the airway adapter.

It is yet another object of the present invention to provide a respiratory component measurement system that includes an airway adapter adapted to be placed in fluid communication with an airway of a patient and a sensor that includes a first element and second element. The first element is in physical communication with the airway adapter, and the second element is adapted to detect an orientation related characteristic of the first element, a motion related characteristic of the of the first element or both. A respiratory component sensor is provided that is adapted to be placed in fluid communication with the airway of a patient.

It is still further object of the present invention to provide a method of method of measuring respiratory component that includes (a) providing an airway adapter adapted to be placed in fluid communication with an airway of a patient, (b) detecting an orientation related characteristic of the airway adapter, a motion related characteristic of the airway adapter, or both, and (c) detecting a respiratory component of a flow of gas through the airway adapter.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1A:
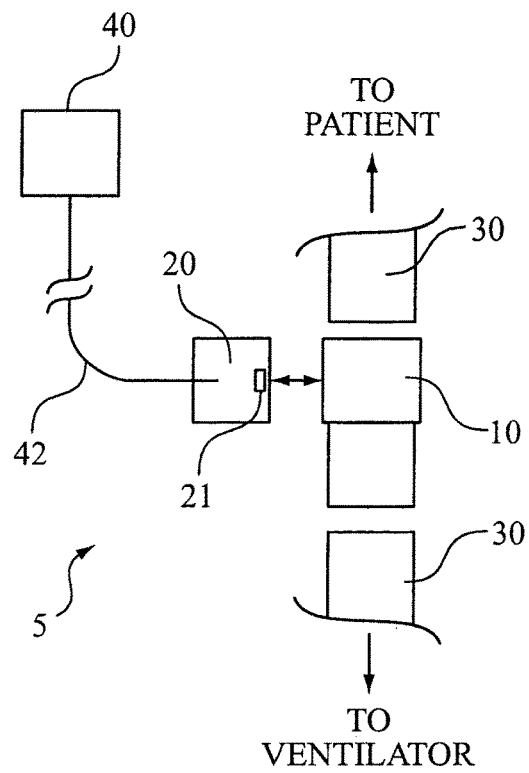
FIGS. 1A-1D are exemplary schematic diagrams of a mainstream respiratory component measurement system showing different positions of an orientation sensor.

The present invention provides a respiratory component measurement system that includes a respiratory component sensor that measures or detects a characteristic associated with the flow of gas through an airway adapter, as well as the ability to detect an orientation related characteristic of the airway adapter, a motion related characteristic of the airway adapter, or both. An orientation related characteristic of the airway adapter is a determination of the tilt or position of the airway adapter in space. In an exemplary embodiment, the orientation related characteristic of the airway adapter is expressed in terms of the location or position of the airway adapter in one or more of the x, y, and z axis. In an similar embodiment, the orientation related characteristic of the airway adapter is expressed in terms of the roll, pitch, and/or yaw of the airway adapter.

The orientation related characteristic can include only one dimension of tilt or position, or it can include more than one dimension of tilt or position. The present invention contemplates that the orientation related characteristic includes an orientation of the airway adapter, a position of the airway adapter, a change of the orientation of the airway adapter, a change of the position of the airway adapter, or any combination thereof.

One exemplary purpose for detecting the orientation related characteristic of the airway adapter is to advise the user of possible misorientation of the airway adapter that could adversely impact on the ability of the airway adapter to provide a reliable and/or accurate measurement of a characteristic associated with a flow of gas through the airway adapter, which is accomplished via a respiratory component sensor adapted to be disposed on the airway adapter.

A motion related characteristic of the airway adapter refers to any force or motion imparted on the airway adapter. Detecting a motion related characteristic includes monitoring and/or measuring the force, or the effect of the force, on the airway adapter. Examples of motion related characteristics include a force, an impact, a shock, a jerk, an impulse, a vibration, an acceleration, a deceleration, a motion or movement of, a change in acceleration, a change in deceleration, a change in motion of the airway adapter, or any combination thereof. Monitoring one or more motion related characteristics of the airway adapter can be done in addition to or in place of monitoring the orientation related characteristic of the adapter. As before, information pertaining to motion related characteristics of the airway adapter can be provided in order to advise the user of possible shocks, vibrations, blows, impacts or other forces that have acted or are acting on the respiratory component measurement system that may impair the ability of the system to produce a reliable and/or accurate measurement.

The respiratory component measurement system of the present invention also provides the ability to communicate the orientation related characteristic, the motion related characteristic of the airway adapter presence of or any combination thereof to a user and/or to a processor. The processor, may use the amount of tilt information, for example, to determine whether the amount of tilt of the airway adapter is outside acceptable bounds. A similar comparison can be done with respect any of the information associated with the orientation related characteristic(s) and/or the motion related characteristic(s).

The present invention contemplates measuring the orientation related characteristic of the airway adapter and/or the motion related characteristic of the airway adapter using any suitable monitoring technique. For example, one or more inclinometers, which are also known as gravitational or tilt sensors, can be used to measure or detect the orientation related characteristic of the airway adapter. Inclinometers measure an angle of an object relative to the Earth's center of gravity. The phrase "tilt sensor" is often used to describe a transducer that measure tilt specifically using gravity as a reference. One suitable sensor for measuring the orientation related characteristic of the airway adapter is a liquid tilt sensor (e.g., mercury switch). A liquid tilt sensor typically outputs binary information (indicating a state of on or off), thus it is only possible to detect when the tilt has exceeded some threshold angle using this type of tilt sensor. The amount of tilt can also be measured using a sensor that detects tilt based on magnetoresistive properties (such as a compass).

The present invention also contemplates using one or more accelerometers to measure the orientation related characteristic of the airway adapter and/or the motion related characteristic of the airway adapter. Accelerometers are well suited for use in the present invention because they have the ability to measure inclination (an orientation related characteristic of the airway adapter) as well as impacts, a change in positions, or movement (motion related characteristics of the airway adapter). More specifically, accelerometers, particularly those with sensitivities around a few g (1 g=9.8 m/sec$^2$), are often used to measure inclination as well as impacts, a change in positions, or movement.

Accelerometers are typically used in one of three modes: (a) as an inertial measurement of velocity and position; (b) as a sensor of inclination, tilt, or orientation in 2 or 3 dimensions, as referenced from the acceleration of gravity (1 g=9.8 m/s2); and (c) as a vibration or impact (shock) sensor.

Accelerometers may produce an analog or digital output. For example, analog accelerometers may output a constant variable voltage depending on the amount of acceleration applied. Digital accelerometers may output a variable frequency square wave often using a method known as pulse-width modulation. Accelerometers may measure in one, two, or three dimensions. The use of single, dual, and tri-axis accelerometers are contemplated by the present invention.

To measure the acceleration of gravity for use as a tilt sensor, an accelerometer having an output range of ±1.5 g is usually sufficient. For use as an impact sensor, ±5 g or more is typically used. For tilt sensing, an accelerometer having a bandwidth of 40-60 Hz is often considered adequate. For vibration measurement or accurate reading of impact forces, the bandwidth of the accelerometer should be in the range of hundreds of Hertz. Any of these types of tilt sensors are suitable for use in the respiratory component measurement system of the present invention.

Accelerometers that utilize capacitive sensing or the piezoelectric effect are also contemplated for use in the present invention. Accelerometers that utilize capacitive sensing output a voltage that is dependent on the distance between two planar surfaces. One or both of these "plates" are charged with an electrical current. Changing the gap between the plates changes the electrical capacity of the system, which can be measured as a voltage output. This method of sensing is known for its high accuracy and stability. Differential capacitance accelerometers, a variant of the general capacitive accelerometer, use differential capacitor sensors, consisting of independent fixed plates and movable "floating" central plates that deflect in response to changes in relative motion. Under acceleration, the deflection of the center plate will cause a difference in the capacitances of the two capacitors on either side of the plate. Again, any of these types of sensors can be used in the respiratory component measurement system of the present invention to measure or detect the orientation related characteristic(s) of the airway adapter and/or the motion related characteristic(s) of the airway adapter.

Additionally, there are other types of accelerometers suitable for use in the present invention, including but not limited to: thermal, null-balance, servo force balance, strain gauge, resonance, magnetic induction, optical, surface acoustic wave (SAW), vibrating beam, and electromagnetic accelerometers. Commercial examples of accelerometers suitable for use in the present invention include single, dual and tri-axis accelerometers from companies such as Hitachi Metals H34C, Analog Devices (e.g. ADXL 105, one axis; ADXL 202, two axes—differential capacitance accelerometers), MEMSIC (e.g. 2125GL 2-axes thermal accelerometer), and Freescale Electronics (e.g. MMA7260Q—3 axes—capacitive accelerometer). Freescale Electronics provides a single device with four user selectable sensitivity ranges (±1.5 g, ±2 g, ±4 g, or ±6 g) which allows it to be toggled between a tilt detection algorithm with a 1.5 g setting and a vibration algorithm at the 6 g setting.

Other continuous inclination sensors are suitable for use in the present invention. Examples of sensors measuring continuous inclination include electrolytic tilt sensors (e.g. Fredericks Company), or using an LED and arrays of photodetectors. Any of these types of tilt sensors are suitable for use in the respiratory component measurement system of the present invention to measure orientation related characteristics of the airway adapter and/or motion related characteristics of the airway adapter.

FIGS. 1A-1D illustrates four exemplary embodiments of a respiratory component measurement system, generally indicated at 5, that includes a sensor 21,22, 23, 24, 25 in physical communication with an airway adapter 10. Sensor 21,22, 23, 24, 25 is a sensor that has the ability to detect and/or measure one or more orientation related characteristics of the airway adapter and/or one or more motion related characteristics of airway adapter 10.

In all of these embodiments, airway adapter 10 is a mainstream airway adapter and is coupled in series with a breathing circuit 30, one end of which is coupled to a ventilator or a pressure/flow generating element, and another end is coupled to an airway of a patient. The breathing circuit is coupled to the airway of the patient using any conventional technique, which includes invasive or non-invasive coupling techniques. The present invention also contemplates that airway adapter 10 is coupled to the airway of the patient, without being coupled to a ventilator or the pressure/flow generator.

In the embodiment illustrated in FIG. 1A, respiratory component measurement system 5 includes a respiratory component sensor 20 adapted to be coupled to airway adapter 10. In this embodiment, a orientation/motion related characteristic sensor 21 is located in respiratory component sensor 20, which is selectively coupled to airway adapter 10. Respiratory component sensor 20 is in communication with a host system 40 via a communication link 42. Communication link 42 can be a hardwired connection, a wireless connection, or a combination thereof. An exemplary orientation/motion related characteristic sensor 21 suitable for use in this configuration is an accelerometer type of sensor.

It can be appreciated that in this embodiment, airway adapter 10 need not include any components needed to detect the orientation of the airway adapter, because the orientation detecting components are carried on the respiratory component sensor that mounts to the airway adapter. Thus, this embodiment is particularly suited for applications in which airway adapter 10 is disposable, i.e., not typically reused. It should be noted that the present invention contemplates fixing sensor 21 to respiratory component sensor 20 in a permanent or non-permanent fashion.

Respiratory component sensor 20 can be any type of sensor capable of measuring a characteristic associated with a flow of gas through airway adapter 10. Exemplary sensors suitable for use the respiratory component sensor include a flow sensor, volume sensor, gas sensor, humidity sensor, temperature sensor, pressure sensor, or any combination thereof. If the respiratory component sensor is a gas sensor, the present invention contemplates that a variety of gas sensors are suitable for use in the present invention, such as an infrared radiation gas sensing system, a luminescence quenching gas sensing system, an electrochemical gas sensing system, or any combination thereof. The gas sensor can be used to measure carbon dioxide, oxygen, nitrogen, nitrous oxide, carbon monoxide, volatile organic compounds, anesthetic agents, trace gases, exhaled breath markers, nitric oxide or any combination thereof.

Figure 1B:
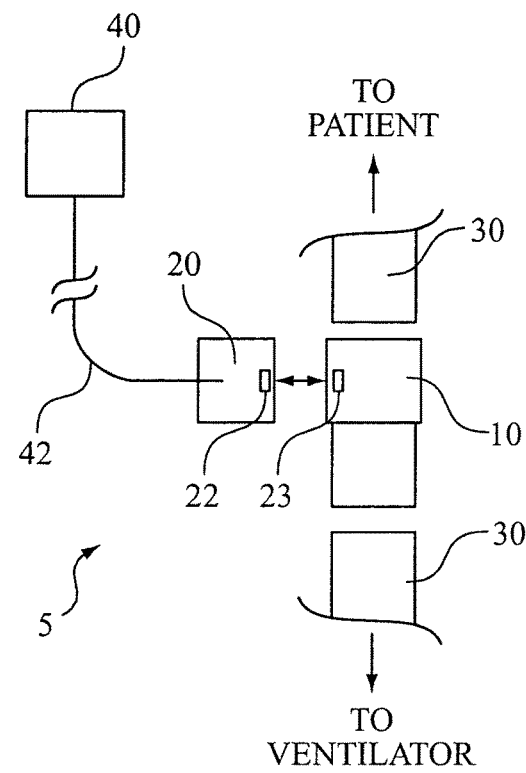

FIG. 1B illustrates a respiratory component measurement system 5 in which airway adapter 10 contains an orientation/motion related characteristic sensor that is defined by two separate components rather than the single component of FIG. 1A. In this embodiment, the orientation/motion related characteristic sensor is defined by a sensing element 23 disposed on airway adapter 10, and a detecting element 22 disposed in respiratory component sensor 20. As in the previous embodiment, respiratory component sensor 20 is either fixed to or selectively attachable to airway adapter 10. In an exemplary embodiment, respiratory component sensor 20 is selectively coupled to the airway adapter. The combination of sensing element 23 and detecting element 22 is used to detect the orientation/motion related characteristics of airway adapter 10. For example, detecting element 22 is used to detect the physical position, orientation, movement, etc. of sensing element 23.

An exemplary embodiment of sensing element 23 suitable for use in this embodiment is a magnet that produces a magnetic field having a detectable orientation. For example, the polarity of sensing element 23 can be used to determine its orientation in space. Sensing element can include multiple magnets disposed at one location or in multiple locations on the airway adapter. Detecting element 22 is any device capable of detecting the magnetic field produced by sensing element 23 and determining the orientation/movement related characteristics of the sensing element based on this detected field. The present invention also contemplates placing one or more magnets on breathing circuit 30 and, when joined with airway adapter 10, the position of the magnet on the breathing circuit can be detected by detecting element 22.

This configuration allows only a passive, relatively simple element, such as sensing element 23 (e.g., a magnet), to be provided on the airway adapter, while the more complex orientation/mutation related characteristic detecting element 22 is provided on respiratory component sensor 20. Thus, this embodiment, like that of FIG. 1A, is particularly suited for applications in which airway adapter 10 is disposable. Of course, it should be noted that the present invention contemplates fixing sensing element 23 to airway adapter 10 and/or breathing circuit 30 in a permanent or non-permanent fashion. That is, the airway adapter and sensing element 23 can be configured such that the orientation sensing element can be readily removed from the airway adapter so that the sensing element can be reused with other airway adapters.

Figure 1C:
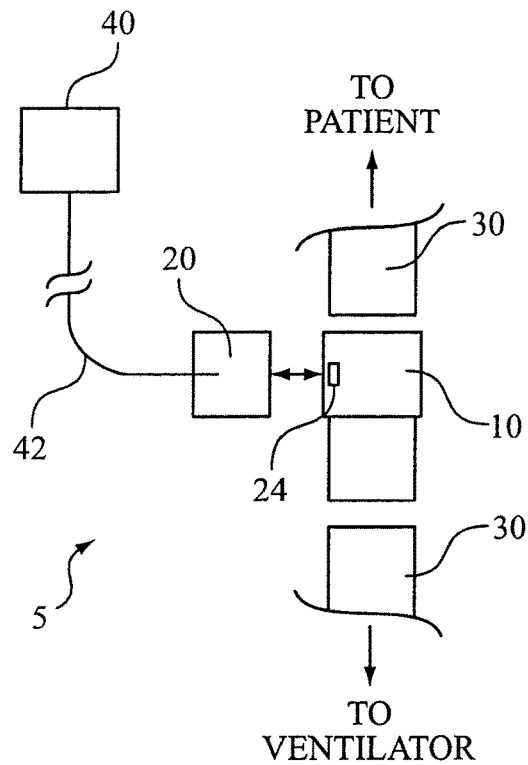

FIG. 1C illustrates a respiratory component measurement system 5 in which an orientation/motion related characteristic sensor 24 is disposed on airway adapter 10. When airway adapter 10 is coupled with respiratory component sensor 20, the orientation/motion related characteristic(s) sensed by the sensor 24 is communicated to the respiratory component sensor via a physical or wireless connection. As in the previous embodiment, airway adapter 10 and orientation/motion related characteristic sensor 24 can be configured such that the orientation sensor can be readily removed from the airway adapter so that the orientation/motion related characteristic sensor can be reused with other airway adapters.

Figure 1D:
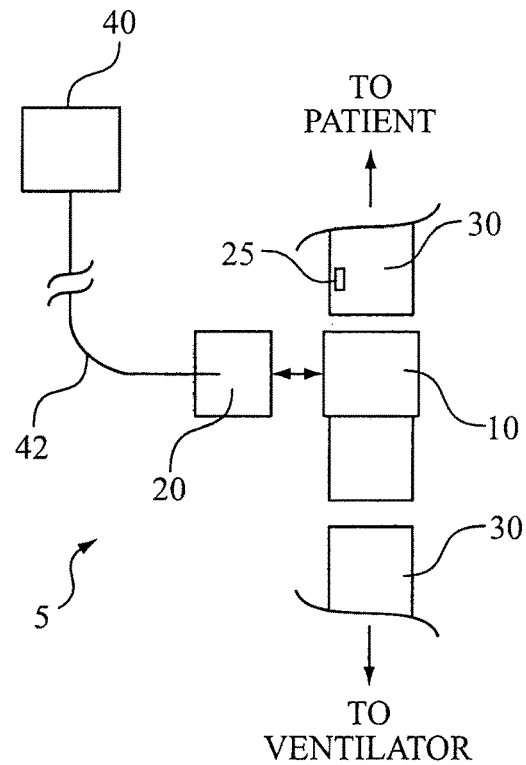

FIG. 1D illustrates a respiratory component measurement system 5 in which airway adapter 10 is coupled to respiratory component sensor 20 and an orientation/motion related characteristic sensor 25 is located in breathing circuit 30. When breathing circuit 30 is assembled with airway adapter 10, the orientation/motion related characteristic information is communicated from to sensor 25 to respiratory component sensor 20.

In the embodiment shown in FIGS. 1A-1D, host system 40 receives the orientation/motion related signals output by orientation/motion related characteristic sensors 21, 24, 25 or orientation/motion related characteristic detecting element 22 and uses this information to detect the orientation/motion related characteristic(s) of the airway adapter, such as the tilt of the airway adapter relative to the earth's gravity. This host system can output the orientation/motion related information using any conventional technique, for example, by displaying the information on a display. The host system can also communicate the orientation/motion related information to a remote location, such as a nurse's station in a hospital or a central monitoring station, using any conventional communication technique or network, including internet communications.

The present invention also contemplates that the host system compares the signal provided by orientation/motion related characteristic sensors 21, 24, 25 or orientation/motion related characteristic detecting element 22 to a threshold value and output an alarm or warning if this signal exceeds the threshold. In addition or alternatively, the host system can discontinue and/or isolate the respiratory component sensor from the breathing circuit and/or airway adapter, for example, by closing the valve communicating the airway adapter to the respiratory component sensor if the orientation signal indicates that the orientation of the airway adapter is outside a predetermined limit.

The present invention also contemplates eliminating host system 40 and providing some or all of the functions that are capable of being performed by the host system in respiratory component sensor 20. In which case, visual, audio, and/or communication outlets would be provided on the respiratory component sensor so that the orientation determination, alarms, warnings, etc. could be output to a user.

Figure 2:
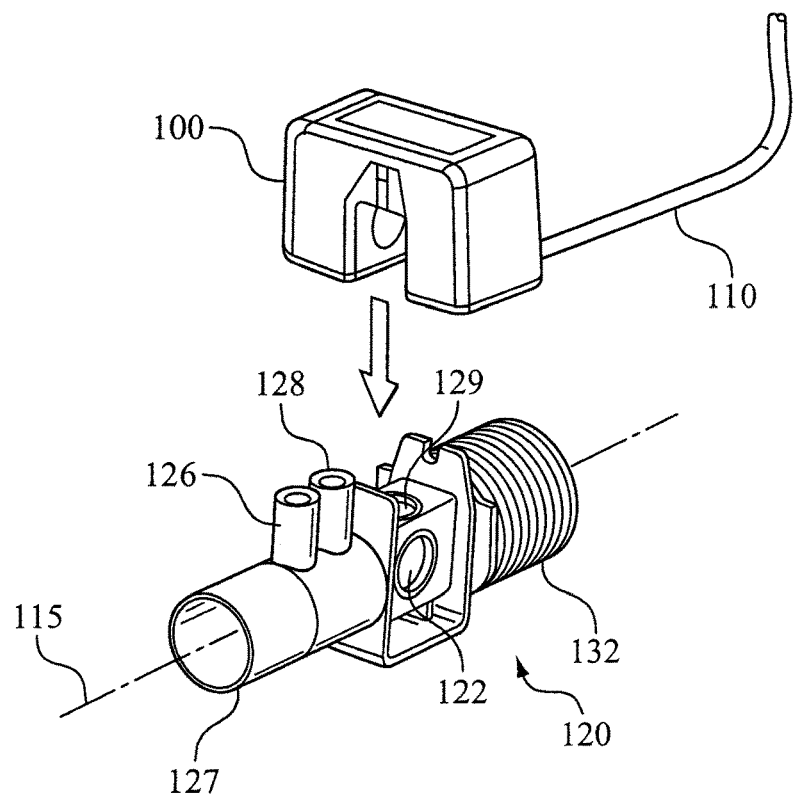
FIG. 2 is a perspective view of an exemplary embodiment of a respiratory component measurement system comprising a respiratory gas component sensor configured to be removably secured to a combination $CO_2/O_2$/flow airway adapter.
Figure 3:
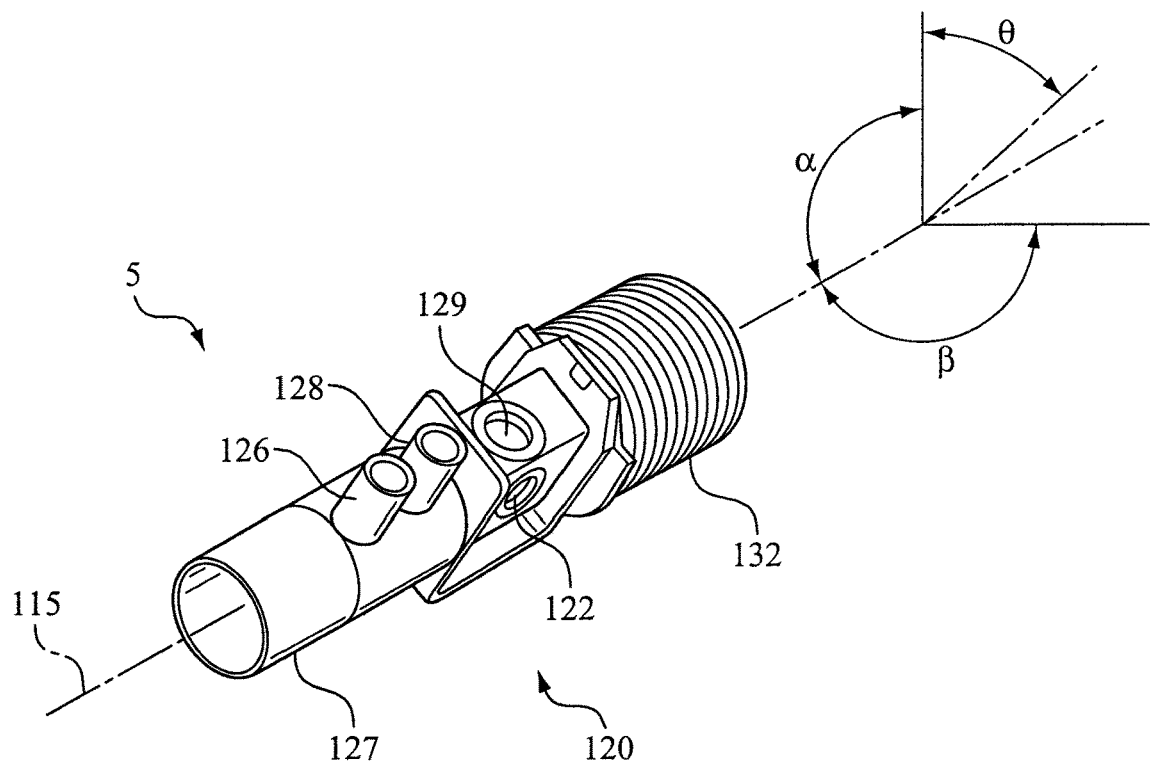
FIG. 3 is a perspective view of the airway adapter in FIG. 1 shown rotated approximately 45 degrees.

An exemplary embodiment of a respiratory component measurement system 5 including an airway adapter 120 and a complementary respiratory component sensor 100 constructed in accordance with and embodying the principles of the present invention are shown in FIGS. 2 and 3. More specifically, FIG. 2 shows a perspective view of a respiratory component measurement system 5 comprising a respiratory gas component sensor 100 and an airway adapter 120 according to the principles of the present invention. Respiratory gas component sensor 100 is coupled to a host system (not shown) via a communication link 110. In this embodiment, respiratory gas component sensor 100 is configured to be removably secured to airway adapter 120, which is a combination $CO_2/O_2$/flow airway adapter adapted to be assembled with a patient breathing circuit (not shown).

A combination $CO_2/O_2$/flow airway adapter is an airway adapter that is capable of providing gas measurements of carbon dioxide ($CO_2$), oxygen ($O_2$), and flow measurements. An airway adapter that has been adapted to measure $CO_2$ via infrared absorption and $O_2$ via luminescence quenching is disclosed in U.S. patent application Ser. No. 09/841,451 to Mace et al. (publication no. 2002/0029003)("the '003 application"), the contents of which are incorporated herein by reference. A gas measurement system that is capable of receiving the above airway adapter is disclosed in U.S. patent application Ser. No. 11/368,832 to Russell (publication no. 2006/0145078)("the '078 application"), the contents of which are incorporated herein by reference.

Respiratory gas component sensor 100 includes a gas sensor for measuring the amount of a gas constituent in the flow of gas passing through the airway adapter. In an exemplary embodiment, respiratory gas component sensor 100 includes a housing that contains an infrared emitter and an infrared detector, which are used to measure $CO_2$. Airway adapter 120 includes at least one window 122 that allows infrared radiation from the infrared emitter to be passed through the flow of gas passing through the airway adapter. In an exemplary embodiment, a second window is disposed on the other side of the airway adapter and opposite window 122 that allows infrared radiation that has passed through the flow of gas flowing through the airway adapter to be directed back a detector in to respiratory gas component sensor 100.

In this embodiment, respiratory gas component sensor 100 also includes a luminescence quenching type of gas sensor, which is typically used to measure $O_2$. The luminescence quenching system includes an excitation radiation source and a luminescence detector disposed in respiratory gas component sensor 100. Airway adapter 120 includes a window 129 through with the excitation radiation passes to excite a luminescable material disposed in the airway adapter in fluid communication with the flow of gas passing through the airway adapter.

Flow is measured via ports 126 and 128. In particular, tubing (not shown) is coupled to ports 126 and 128. The other end of the tubing is coupled to a pressure sensor that provides a differential pressure measurement between the sides of a flow restriction contained in the airway adapter. The differential pressure on either side of the flow restriction is used to determine the rate of flow of gas through the airway adapter. In this exemplary embodiment, the flow measuring components and the gas sensing components of airway adapter 120 are arranged in a side-by-side or serial configuration.

Airway adapter 120 is typically assembled in a breathing circuit between an elbow, which is connected to a patient interface, such as a mask or endotracheal tube, and "Y" piece, which is connected to a positive pressure generator, such as a ventilator. For example, the present invention contemplates coupling a distal end section 127 to the patient interface and coupling a proximal end section 132 to the "Y" piece or other portion of the breathing circuit.

In an exemplary embodiment of the present invention, the host system provides the power to the respiratory gas component sensor, receives the gas concentration signal, and derived measurements output from the respiratory gas component sensor. In the case where the gas concentration signal is the carbon dioxide concentration signal, the host system displays measurements, such as (a) the concentration of carbon dioxide in a patient's exhalations, (b) inspired carbon dioxide, (c) respiration rate, and/or (d) end tidal carbon dioxide.

The present invention also contemplates that the respiratory component gas sensor may be battery powered, with either an integrated or separate battery pack. Communication to the host system can be done wirelessly or via a hardwired connection to the host system. Wireless communications using protocols known in the art such as Bluetooth, Zigbee, UWB used in body area networks (BAN) and personal area networks (PAN) are contemplated. The respiratory gas component sensor may also be connected via a cable to a hub, which integrates the signals from the gas measurement system with other physiological measurements.

The present inventors recognized that it is helpful in order to ensure proper operation of the gas flow/sensing system of the present invention, that airway adapter 120 be maintained in an orientation that is substantially vertically upright in space as shown in FIG. 2. If the position of airway adapter 120 is sufficiently perturbed from the substantially vertical upright position, as shown in FIG. 3, then the measurements obtained from respiratory gas component sensor 100, as well as those from the flow sensing portion of airway adapter 120, could be degraded. For example if airway adapter 120 is rotated (rolled) by angle θ from the substantially vertically upright position about a longitudinal axis 115 such that angle θ exceeds a predetermined threshold, airway adapter 120 would be more susceptible to fluids adversely affecting the gas and/or flow measurements. For example, fluids may accumulate on window 122 making the gas constituent measurement made using this window unreliable and/or inaccurate.

In addition, the orientation shown in FIG. 2 minimizes water entry into pressure sensing tubing via ports 126 and/or 128, and/or water accumulation on windows 122 or 129. The embodiment illustrated in FIG. 3 shows an angular tilt of approximately 45 degrees from longitudinal axis 115. For example, for angular tilts from longitudinal axis 115 greater than 45 degrees, i.e., Θ>45°, $CO_2$ measurement windows 122, and the oxygen sensing window/film 129, and the pressure sensor (via the sensing tubing) are more vunerable to the exposure of liquids or ingress of those liquids. In the embodiment shown the angular tilt is sensed by an orientation sensor (not shown) within respiratory gas component sensor 100. To sense the rotation (i.e. roll) about longitudinal axis 115, a sensor that responds to or detects a change in position in one axis of rotation can be used. Of course, such a sensor would have to be positioned so as to be able to detect the rotation of airway adapter 120.

The present invention also contemplates using a sensor which monitors changes in three-dimensional space. Besides the degree of roll, the amount of pitch designated by the angle α in FIG. 3 and yaw designated by the angle β in FIG. 3 can be sensed as well. Note however in this example the sensor is only experiencing roll.

It is contemplated that thresholds for acceptable angles or position in space can be either pre-defined, user defined, automatically set, or set manually. Experiments on the bench or in the clinical setting can be used to determine that these thresholds should be. Additionally, these thresholds can be fuzzy in nature such that the indication to the host system or user could be of increasing or decreasing urgency if the position changed. The thresholds could be set by the clinical. For example, if the clinician finds that a certain position results in sputum or fluid interfering with a measurement, that position could be indicated to respiratory gas component sensor 100 via a host system and the threshold adjusted accordingly.

In addition the thresholds used to compare to the orientation/motion related characteristics to determine whether they are within acceptable levels can also be changed dynamically. For example, the present invention contemplates providing a humidity sensor to sense the moisture content of the gas flowing through the airway adapter. The threshold can be set based on the output of the humidity sensor. For example, if the gas has a relatively high humidity, a threshold can be lowered so that less tilt is tolerated before an unacceptable level of tilt is reached.

Figure 4:
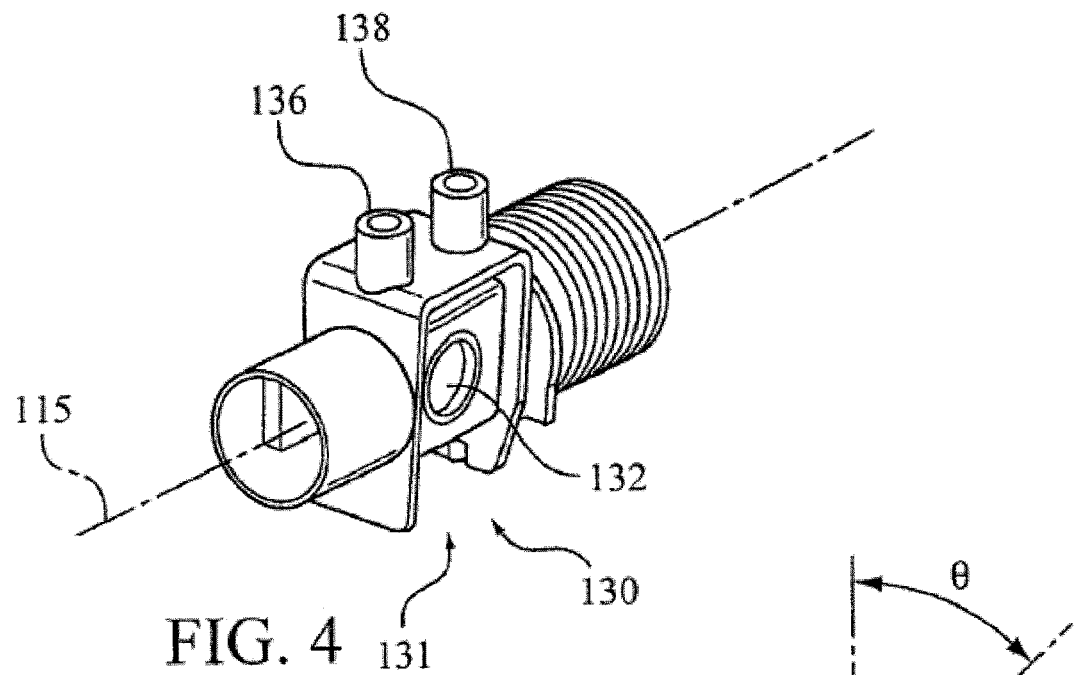
FIG. 4 is perspective view of an exemplary embodiment of a respiratory component measurement system comprising a respiratory gas component sensor configured to be removably secured to a combination $CO_2$/flow airway adapter.
Figure 5:
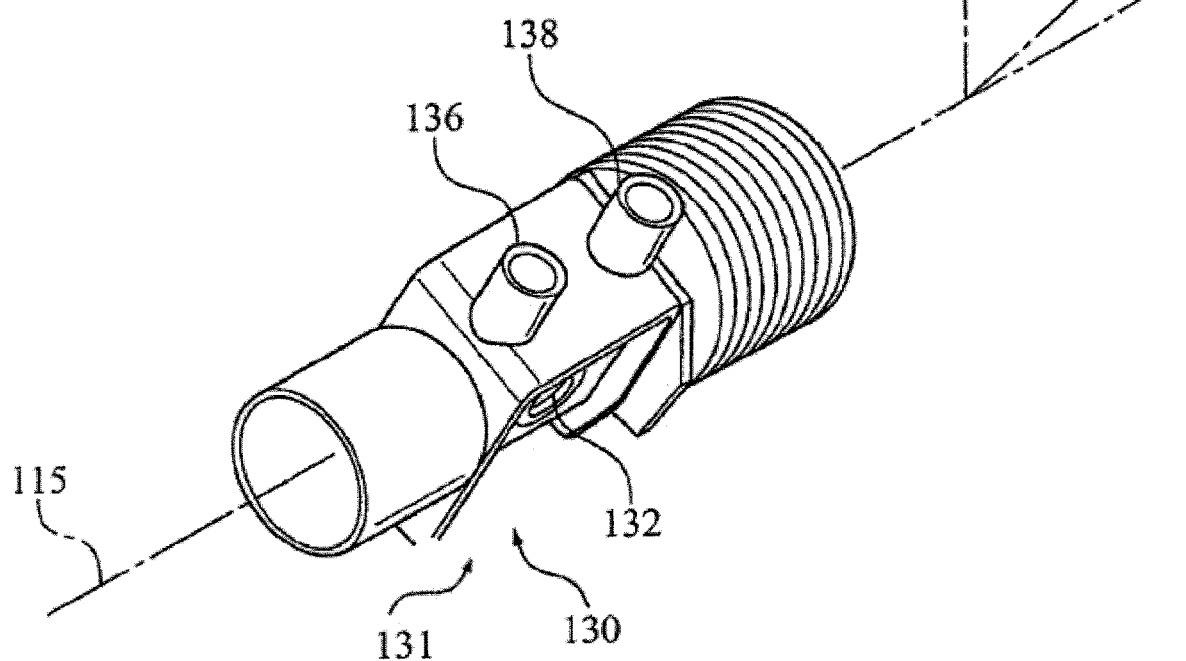
FIG. 5 is a perspective view of the airway adapter in FIG. 3 shown rotated approximately 45 degrees.

FIGS. 4 and 5 illustrate another exemplary embodiment of an airway adapter 130 suitable for us in respiratory component measurement system 5 of the present invention. This type of airway adapter is also disclosed in the '003 application. As in the previous embodiment, a respiratory component sensor (not shown) is coupled to airway adapter 130, as indicated by arrow 131. In this embodiment, airway adapter 130 is a combination $CO_2$/flow airway adapter. The flow sensing components, which include ports 136 and 138, are arranged in parallel with the gas components of the airway adapter, which includes window 132.

Figure 6A:
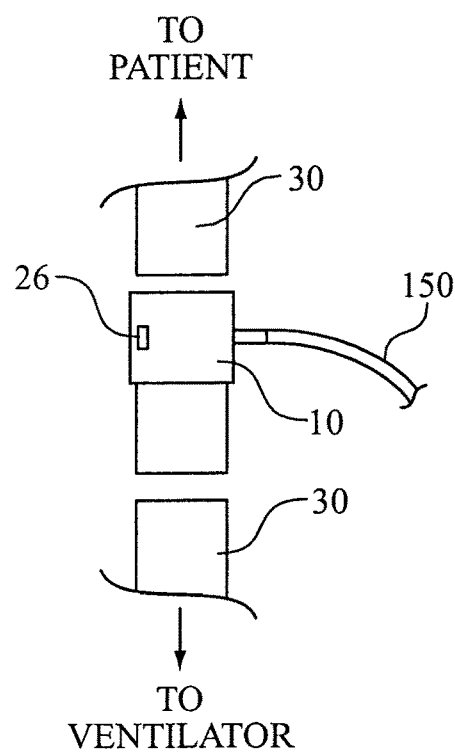
FIGS. 6A and 6B are exemplary schematic diagrams of a sidestream respiratory component measurement system showing different positions of the orientation sensor.
Figure 6B:
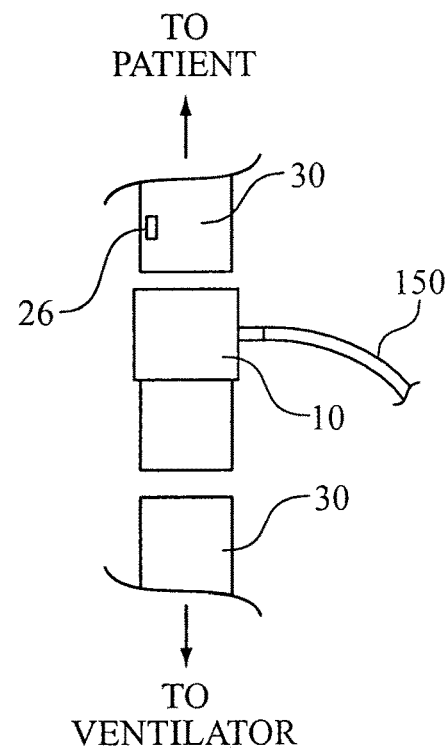

FIGS. 6A and 6B schematically illustrate a sidestream respiratory component measurement system according to the principles of the present invention. These figure show different arrangements for the location of an orientation/motion related characteristic sensor 26 in such a system. Sidestream respiratory component measurements and systems for conducting such measurements are disclosed in U.S. Pat. No. 6,954,702 to Pierry et. al ("the '702 patent) the contents of which are incorporated herein by reference.

A sidestream gas measurement system includes a sample cell in fluid communication with an airway of a patient via a tube 150. In an embodiment shown in the '702 patent, a sample cell is selectively attachable to a housing. More specifically, a sample cell connector in the form of a receptacle is provided in the housing to allow the sample cell to selectively attach to the housing such that the sample cell is in alignment with the components of a gas sensor provided in the housing. An airway adapter 140 is connected in line with the breathing circuit 30 so as to connect or communicate a sampling tube 150 to the breathing circuit.

A pump is typically provided to draw the gas into the sample cell from the gas sample site. As is the case in a conventional sidestream system, a gas sensor outputs a signal indicative of a property of a gas in the sample cell. This signal is provided to a gas monitor, which processes the signal to determine a respiratory gas variable based on the signal. A processor receives the respiratory gas variable and communicates it to a host system via a communication link. The communication link is either hardwired or wireless.

In FIG. 6A, orientation/motion related characteristic sensor 26 is disposed on airway adapter 10 and is in communication with either the respiratory component sensor or a host system via physical connection (not shown) or via a wireless communication. In FIG. 6B, orientation/motion related characteristic sensor 26 is coupled to a patient circuit 30 and is in physical communication or wireless communication with the respiratory component sensor or host system.

Figure 7:
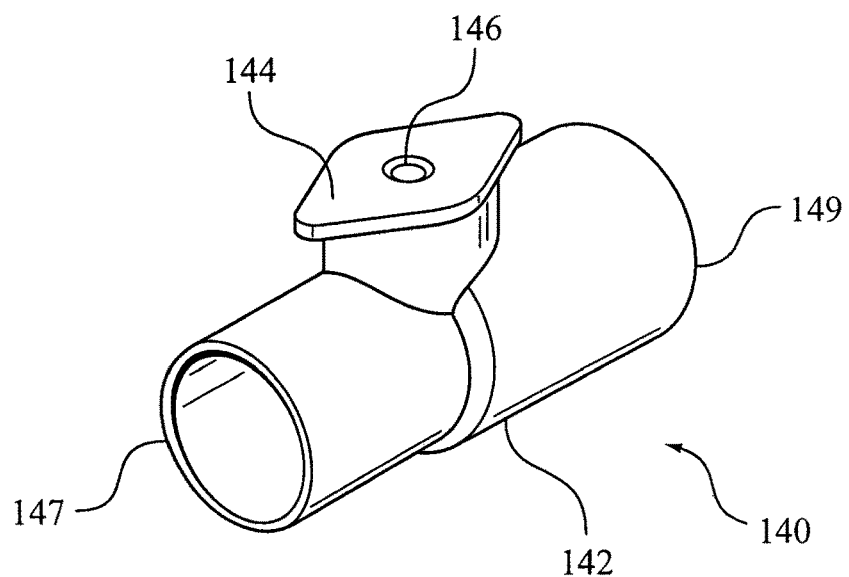
FIG. 7 is perspective view of a sidestream sampling airway adapter.

FIG. 7 illustrates a sidestream sampling airway adapter 140 suitable for use in respiratory component measurement system 5. Airway adapter 140 includes a proximal end section 149 and a distal end section 147 that interface with the breathing circuit. A cap 144 is coupled to a body 142 of the airway adapter and forms a sampling port from which the sidestream flow of gas is drawn from the airway adapter. An opening 146 is defined in cap 144 for connecting the sampling tube (not shown) to the airway adapter. Sidestream sampling airway adapters suitable for use in respiratory component measurement systems are disclosed in U.S. Pat. Nos. 6,935,338 and 7,059,322, the contents of which are incorporated herein by reference.

The present invention contemplates that the orientation/motion related characteristic sensor is located in physical communication with sidestream airway adapter 140. It may be within cap 144 or attached to or within a component that is assembled in use with the sidestream sampling airway adapter. In an exemplary embodiment, the orientation/motion related characteristic sensor requires very low power and may include its own power source and means for transmitting its output to a nearby receiver within a host system or component of a host system.

Figure 8:
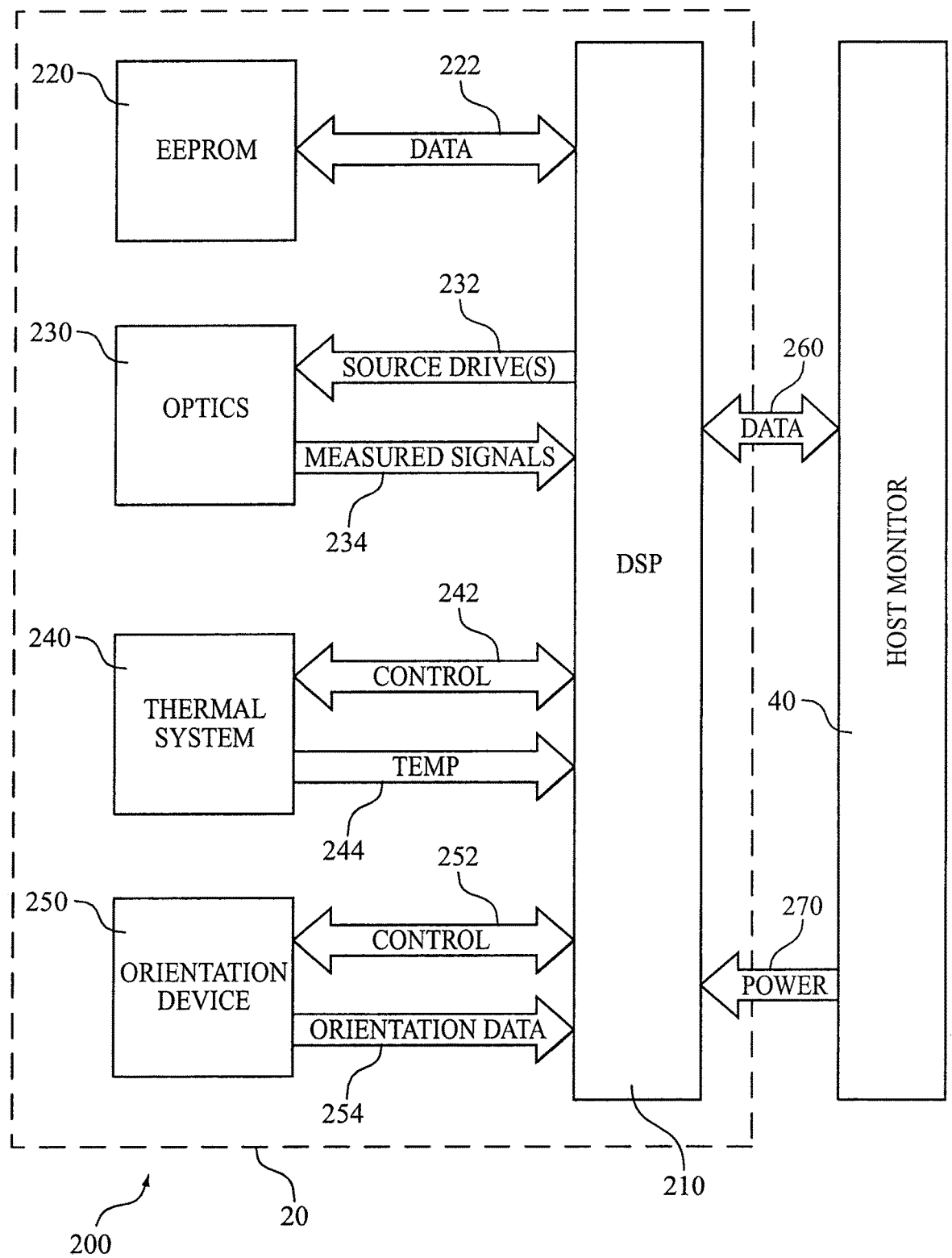
FIG. 8 is a block diagram of an exemplary respiratory component measurement system.

FIG. 8 is a block diagram an exemplary embodiment of a circuit architecture 200 suitable for use in respiratory component measurement system 5. Circuit architecture 200 includes signal processing and control elements/electronics that are used to measure and compute values for infrared absorbing gases, such as carbon dioxide, and/or luminescence quenching gases, such as oxygen. These computations can be done continuously, i.e., during each processing cycle for the circuit, intermittently, e.g., at predetermined intervals, or only when requested. In the embodiment shown in FIG. 8, the signal processing and control elements/electronics are shown disposed in respiratory component sensor 20. It is to be understood, however, that these components may also be disposed in a host system 40, or they may be distributed between the host system and sensor 20.

The exemplary circuit architecture 200 shown in FIG. 8 includes all the signal processing and control electronics and takes advantage of highly integrated digital signal processing (DSP) technology required to perform many of the complex electronic interface functions within a small single chip processor that includes program and data storage as well as analog to digital conversion. The placement of a DSP within respiratory component sensor 20 enables an easy interface of the control circuitry to the orientation measurement devices.

Circuit architecture 200 includes a processor 210 that provides control, measurement, and signal processing functions. An exemplary processor suitable for use in the present invention is the TMS320F2812 DSP, manufactured by Texas Instruments. Processor 210 provides source timing signals 232 to an infrared source and visible light LEDs (e.g. green or blue LEDs) for luminescence quenching measurements. Such LEDs are located in an optical assembly 230. Executable programs and data are stored in a memory 220 that communicates with processor 210 via link 222. Data signals 234 from the infrared detector, which receives the transmitted infrared radiation after it passes through the windows of the airway adapter, and the visible light detectors, which receive reflected and scattered visible light from the quenching process are amplified prior to analog to digital conversion within processor 210. The low level signals from the detectors are AC coupled, amplified, and level shifted to allow for complete signal acquisition.

In the exemplary embodiment, circuit 200 also includes a thermal system 240 that regulates separately the temperature of the infrared detectors and heaters in physical communication with the luminescence sensing film. This regulation is accomplished using control signals 242 from processor 210 and temperature signals 244 to the processor.

Processor 210 communicates data bi-directionally via a data link 260 with host monitor 40. Datalink 260 can be a wireless link, a hardwired link, or a combination thereof. The present invention also contemplates providing an input/output device directly on respiratory component sensor 20 so that the date output from the processor can be displayed on the sensor head.

In this embodiment, host monitor 40 provides power, via a power coupling 270, to respiratory component sensor 20 including circuit 200. It is to be understood, that the present invention also contemplates providing a power supply, such as a battery or plurality of batteries, in sensor head 20, thereby eliminating the need for power coupling 270.

An orientation/motion related characteristic sensor 250, which in the exemplary device is an accelerometer, is controlled by processor 210 via control lines 252 and communicates orientation/motion related data 254 to the processor. In the exemplary embodiment a small, low-cost, 3-axis accelerometer is used in respiratory component sensor 20 as the orientation/motion related characteristic sensor. Respiratory component sensor 20 also measures carbon dioxide with infrared absorption, oxygen with luminescence quenching, and flow by means of differential pressure sensing. Software running on processor 210 interfaces with the accelerometer and permits monitoring of the orientation/motion related characteristics of the respiratory component sensor 20, such as tilt. If the monitored orientation/motion related characteristics exceed a predetermined amount, for example if the tilt in any of the three axes exceed a predetermined amount, a message or alarm is communicated to the host monitor. The host monitor alerts the user via the host system display or other indicating element that the tilt has exceed acceptable levels. The use can then reposition the airway adapter, and the respiratory component sensor attached thereto, to correct the amount of tilt.

The present invention contemplates displaying a "tilt" indicator if the airway adapter remains in the "tilted" position for greater than a determined amount of time, and if breathing is detected via the $CO_2$ and/or flow for greater than a predetermined amount of time (several minutes for example). For example, acceptable position may be defined by a cone in the X,Y,Z space, and if the position of the sensor is outside that defined cone, then an error message or other warning could be generated.

The present invention also contemplates using visual indicators positioned either on the airway adapter or respiratory component sensor to indicate to the user when the position of the airway adapter needs to be reoriented or is in an acceptable position. This may be accomplished with visual indicators, including but not limited, to a single LED, multiple LEDs, and a small LCD. For example, a red LED may be illuminated when the airway adapter is mal-positioned and upon repositioning into an acceptable position, a green LED would be illuminated. Audio indicators are contemplated as well. This may be accomplished with known methods of sound generation.

Additionally, depending upon the type of respiratory component sensor or type of airway adapter adapted with the respiratory component sensor, different cones or ranges of acceptability for the orientation/motion related characteristics can be defined. For example, a respiratory component sensor interfaced with airway adapters shown in FIGS. 2-3 would define an acceptability space that would be a mirror along the substantially vertical-axis of a respiratory component sensor interfaced with airway adapters shown in FIG. 4-5. An airway adapter such as that shown in FIGS. 2-3 positioned in the defined acceptability space, such as shown in FIG. 2, minimizes the ingress of fluids into the pressure sensing ports and accumulation of fluids on the windows for infrared sensing and luminescence based gas measurements.

Exemplary embodiments of the present invention contemplate using an accelerometer to determine orientation/motional related characteristics. In sensing motion related characteristics, the accelerometer may monitor parameters such as free-fall and shock. Given the potentially small size of respiratory component sensor 20 and its location at the end of cable, it is prone to be dropped and/or banged onto hard surfaces. Provided the orientation/motion related characteristic sensor is powered, software can monitor the occurrences of motion related characteristics, such as vibration, impact, free-fall, jerk, impulse, and shock and either store the history in the EEPROM or communicate this information to a host monitor. The number, magnitude and type of occurrence of motion related characteristics could be stored as well. This information can be used for servicing/warranty and possibly for advice to the user.

The present invention contemplates that thresholds for acceptable occurrences of motion related characteristics can be either pre-defined, user defined, automatically set, or set manually. Multiple thresholds are contemplated as well including one threshold for warning the user or operator and a second threshold for alarming or even disabling the operation of the system. For example, if the shock exceeded a predetermined number of g's known to consistently cause damage to the device then it may be advisable to disable the operation of the device if such a shock was measured. Additionally, the monitoring of motion related characteristics would be applicable to sidestream systems.

The features of the present invention has a number of advantages including increased reliability and user confidence in the measurement system and the basic measurement under adverse conditions and the ability to automatically assess potential damage to the device (e.g. shocks greater than 5 g's) etc. Additionally, the presence of accelerometer permits the monitoring of system vibrations. It is contemplated that these measured vibrations originating from either the patient or ventilator could be used for diagnostic purposes such detection of abnormal breathing patterns (e.g. wheezing, asynchrony), or ventilator diagnostics (malfunctioning valve etc).

Additionally, the present inventions includes configurations comprising mainstream flow and sidestream gas portions as well as mainstream gas with sidestream gas portions. Also a respiratory component sensor which includes gas components and a flow component with an orientation sensor is contemplated. U.S. provisional patent application No. 60/808,312 to Russell, the contents of which are incorporated herein by reference, describes a respiratory component sensor which includes both respiratory gas and flow components. U.S. Pat. No. 6,691,579, the contents of which are incorporated herein by reference, describes respiratory gas component sensor and clip-on flow component.

The motional related information can be monitored and used to control the respiratory component measurement system and/or make recommendations with respect to the respiratory component measurement system. For example, the number, frequency, and/or magnitude of the shocks, impacts, accelerations, decelerations can be monitored and tracked. This information can be compared to acceptable threshold, and, depending on the result of this comparison, use to disable the respiratory component measurement system or components thereof, provide warnings to the user, or make recommendations to the user, such as take the system in for repair and/or inspection.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory component measurement system comprising:
    an airway adapter adapted to be in fluid communication with an airway of a patient;
    a sensor element in physical communication with the airway adapter,
    the sensor element being configured to detect:
        a rotational angle of the airway adapter relative to an axis to produce an orientation signal indicating the detected rotational angle of the airway adapter relative to the axis; and
        at least one of a force, an impact, a blow, a shock, a jerk, an impulse and a vibration imparted on the airway adapter to produce a motion signal indicating the at least one detected fore, impact, blow, shock, jerk, impulse and vibration imparted on the airway adapter;
    a respiratory component sensor disposed on the airway adapter and adapted to measure a characteristic associated with a flow of gas through the airway adapter; and
    a processor coupled to the sensor element to receive one of the orientation signal or the motion signal and configured to determine:
        the orientation signal exceeding an orientation threshold that is set based on the measured characteristic associated with the flow of gas through the airway adapter; and
        the motion signal exceeding a motion threshold.

2. The system according to claim 1, wherein the respiratory component sensor is at least one of a flow sensor, a volume sensor, a gas sensor, a humidity sensor, a temperature sensor and a pressure sensor.

3. The system according to claim 2, wherein the respiratory component sensor is a gas sensor including at least one of an infrared radiation gas sensing system, a luminescence quenching gas sensing system and an electrochemical gas sensing system.

4. The system according to claim 2, wherein the respiratory component sensor is a gas sensor configured to measure at least one of carbon dioxide, oxygen, nitrogen, nitrous oxide, carbon monoxide, volatile organic compounds, anesthetic agents, trace gases, exhaled breath markers and nitric oxide.

5. The system according to claim 1, wherein the respiratory component sensor includes:
    a gas sensor; and
    a sample tube coupled to the airway adapter and the gas sensor so as to communicate a gas sample from the airway adapter to the gas sensor.

6. The system according to claim 1, wherein the respiratory component sensor is integral with the airway adapter.

7. The system according to claim 6, where the sensor element is disposed within the respiratory component sensor.

8. The system according to claim 1, wherein the sensor element includes one of an accelerometer, an inclinometer, an electrolytic sensor, a liquid tilt sensor, and a magnetoresistive sensor.

9. The system according to claim 1, wherein the processor is programmed
    to produce an indication when the motion signal exceeds the motion threshold.

10. The system according to claim 1, further comprising:
    a host system; and
    a communication link between the host system and the sensor element, wherein the communication link is at least one of hardwired and wireless.

11. The system according to claim 1, wherein the orientation signal indicates the rotational angle of the airway adapter relative to a longitudinal axis of the airway adapter.

12. A respiratory component measurement system comprising:
    an airway adapter adapted to be in fluid communication with an airway of a patient;
    a sensor comprising a first element and a second element, wherein the first element is in physical communication with the airway adapter, and
        wherein the second element is configured to detect:
            a rotational angle of the first element to produce an orientation signal indicating the detected rotational angle of the first element; and
            at least one of a force, an impact, a blow, a shock, a jerk, an impulse and a vibration imparted on the first element to produce a motion signal indicating the at least one detected fore, impact, blow, shock, jerk, impulse and vibration imparted on the airway adapter;
    a respiratory component sensor disposed on the airway adapter and adapted to measure a characteristic associated with a flow of gas through the airway adapter; and
    a processor coupled to the sensor element to receive one of the orientation signal or the motion signal and configured to determine:
        the orientation signal exceeding an orientation threshold that is set based on the measured characteristic associated with the flow of gas through the airway adapter; and
        the motion signal exceeding a motion threshold.

13. The system according to claim 12, wherein the respiratory component sensor is at least one of a flow sensor, a volume sensor, a gas sensor, a humidity sensor, a temperature sensor and a pressure sensor.

14. The system according to claim 13, wherein respiratory component sensor is a gas sensor including at least one of an infrared radiation gas sensing system, a luminescence quenching gas sensing system and an electrochemical gas sensing system.

15. The system according to claim 13, wherein the respiratory component sensor is a gas sensor configured to measure at least one of carbon dioxide, oxygen, nitrogen, nitrous oxide, carbon monoxide, volatile organic compounds, anesthetic agents, trace gases, exhaled breath markers and nitric oxide.

16. The system according to claim 12, further comprising a sample tube coupled to the airway adapter to convey a gas sample to the respiratory component sensor.

17. The system according to claim 12, wherein the respiratory component sensor is integral with the airway adapter.

18. The system according to claim 17, where the second element is disposed within the respiratory component sensor.

19. The system according to claim 12, wherein the first element and second element are magnetoresistive elements.

20. The system according to claim 12, wherein the processor is programmed
to produce an indication when the motion signal exceeds the motion threshold.

21. The system according to claim 12, further comprising:
a host system; and
a communication link between the host system and the sensor element, wherein the communication link is at least one of hardwired and wireless.

22. The system according to claim 12, wherein the orientation signal indicates the rotational angle of the first element relative to a longitudinal axis of the airway adapter.

23. A respiratory component measurement system comprising:
an airway adapter adapted to be in fluid communication with an airway of a patient;
sensing means positioned relative to the airway adapter for detecting:
a rotational angle of the airway adapter relative to an axis to produce an orientation signal indicating the detected rotational angle of the airway adapter; and
at least one of a force, an impact, a blow, a shock, a jerk, an impulse and a vibration imparted on the airway adapter to produce a motion signal indicating the at least one detected fore, impact, blow, shock, jerk, impulse and vibration imparted on the airway adapter;
a respiratory component sensing means operatively coupled to the airway adapter for measuring a characteristic associated with a flow of gas through the airway adapter; and
a processor coupled to the sensing means to receive one of the orientation signal or the motion signal and configured to determine:
the orientation signal exceeding an orientation threshold that is set based on the measured characteristic associated with the flow of gas through the airway adapter; and
the motion signal exceeding a motion threshold.

24. The system according to claim 23, wherein the respiratory component sensing means is at least one of a flow sensor, volume sensor, gas sensor, humidity sensor, temperature sensor and pressure sensor operatively coupled to the airway adapter.

25. The system according to claim 24, wherein the respiratory component sensing means is a gas sensor including an infrared radiation gas sensing system, a luminescence quenching gas sensing system and an electrochemical gas sensing system.

26. The system according to claim 24, wherein the respiratory component sensing means is a gas sensor that measures at least one of carbon dioxide, oxygen, nitrogen, nitrous oxide, carbon monoxide, volatile organic compounds, anesthetic agents, trace gases, exhaled breath markers and nitric oxide.

27. The system according to claim 23, further comprising a sample tube coupled to the airway adapter so as to convey a gas sample to the respiratory component sensing means.

28. The system according to claim 23, wherein the respiratory component sensing means is integral with the airway adapter.

29. The system according to claim 23, where the sensing means is disposed in the respiratory component sensing means.

30. The system according to claim 23, wherein the sensing means includes at least one of an accelerometer, an inclinometer, an electrolytic sensor, a liquid tilt sensor, and a magnetoresistive sensor.

31. The system according to claim 23, wherein the processor is programmed to produce an indication when the motion signal exceeds the motion threshold.

32. The system according to claim 23, further comprising:
a host system; and
a communication link between the host system and the sensing means, wherein the communication link is at least one of hardwired and wireless.

33. The system according to claim 23, wherein the orientation signal indicates the rotational angle of the airway adapter relative to a longitudinal axis of the airway adapter.

* * * * *